United States Patent [19]
Ellis et al.

[11] Patent Number: 5,942,394
[45] Date of Patent: Aug. 24, 1999

[54] DETECTION OF PROTOZOAN PARASITES

[75] Inventors: John Timothy Ellis, Hornsby; Dallas John McMillan, Erskineville, both of Australia

[73] Assignee: Insearch Limited, Haymarket, Australia

[21] Appl. No.: 08/852,407

[22] Filed: May 7, 1997

[30] Foreign Application Priority Data

Aug. 26, 1996 [AU] Australia .............................. PO1883/96

[51] Int. Cl.⁶ .............................. C12Q 1/68; C12P 19/34
[52] U.S. Cl. .............................................. 435/6; 435/91.2
[58] Field of Search ....................... 435/6, 91.2; 536/23.1

[56] References Cited

FOREIGN PATENT DOCUMENTS 3107693  7/1993  Australia .

OTHER PUBLICATIONS

Holmdahl et al., *Parasitology*, 112 (1996), pp. 177–182.
Payne et al., *International Journal of Parasitology*, 26 (1996), pp. 347–351.
Guay et al., *Journal of Clinical Microbiology*, 31 (1993), pp. 203–207.
Dragon et al., "Quality Control of Polymerase Chain Reaction" in *Diagnostic Molecular Biology: Principles and Applications* (Persing et al.), pp. 160–168, American Society for Microbiology.
Guay et al., *J. Clin. Microbiology*, 31:2, Feb. 1993, pp. 203–207.
Holmdahl, *Parasitology*, 112, 1996, pp. 177–182.
Payne et al., *International Journal of Parasitology*, 26:4, 1996, pp. 347–351.
Joss et al., *J. of Medical Microbiology*, 38, 1993, pp. 38–43.
Liesenfield et al., *Journal of Infection*, 29, 1994, pp. 133–138.
Johnson et al., *Biochemical Society, Transactions*, vol. 18, No. 4, Aug. 1990, p. 665.
Guy et al., *Concise Communications*, 172, Jul. 1995, pp. 319–322.
Ostergaard et al., *Immunology and Infectious Diseases*, 5, 1995, pp. 59–66.
Savva et al., "Letters to the Editor: PCR to Detect Toxoplasma," *The Lancet*, 336:8726, Nov. 24, 1990, p. 1325.
Ho–Yen et al., *Journal of Clinical Pathology*, 45, 1992, pp. 910–913.
Edlind et al, *Gene* (Amst) 96(2): 289–249, 1990.
Katiyar et al, *Gene* (Amst) 152: 27–33, 1995.

*Primary Examiner*—Eggerton A. Campbell
*Attorney, Agent, or Firm*—Rothwell, Figg, Ernst & Kurz

[57] ABSTRACT

Method of detecting a protozoan parasite in a sample containing the parasite, the method comprising the steps of: (a) adding to the sample a pair of flanking oligonucleotide primers, at least one flanking primer being specific for and each being complementary to an opposite strand of a double stranded DNA molecule encoding the ITS1 of the protozoan parasite and flanking a region of the ITS1; (b) further adding to the sample a pair of nested oligonucleotide primers, each nested primer being specific for and complementary to an opposite strand of the DNA encoding the ITS1 of the protozoan parasite, the nested primers being complementary to the region of the ITS1 spanned by the flanking primers; (c) providing buffers, reagents, nucleotides and a thermostable DNA polymerase to the sample to form a reaction mixture; (d) heating the sample to a temperature such that the double stranded DNA encoding the ITS1 of the protozoan parasite denatures to form single stranded DNA molecules; (e) cooling the denatured sample to a temperature such that only the flanking primers anneal to their respective complementary sequences on the denatured DNA molecules; (f) heating the denatured and annealed sample to a temperature such that the DNA polymerase extends the primers to form new double stranded DNA molecules spanning the region of the ITS1 defined by the flanking primers; (g) repeating steps (d), (a) and (f) such that the number of copies of the region of DNA encoding the ITS1 region is amplified; (h) heating the sample to a temperature such that the newly amplified double stranded DNA encoding the ITS1 region denatures to form single stranded DNA molecules; (i) cooling the denatured sample to a temperature such that only the nested primers anneal to their respective complementary sequences on the denatured DNA; (j) heating the denatured and annealed sample to a temperature such that the DNA polymerase extends the primers to form new double stranded DNA molecules spanning the region of the ITS1 defined by the nested primers; (k) repeating steps (h), (i) and (j) such that the number of copies of the region of DNA is amplified; and (l) detecting the amplified DNA.

36 Claims, 5 Drawing Sheets ns of the invention consists in a method

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CATTCACAGT CCTTATTCTT TA      22

(2) INFORMATION FOR SEQ ID NO:2:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

CGCTGCTTCC AATATTG      17

(2) INFORMATION FOR SEQ ID NO:3:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

TCCATTGGAG AGATTTG      17

(2) INFORMATION FOR SEQ ID NO:4:

(i) SEQUENCE CHARACTERISTICS:
      (A) LENGTH: 19 base pairs
      (B) TYPE: nucleic acid (C) STRANDEDNESS: single
            (D) TOPOLOGY: linear (ii) MOLECULE TYPE: cDNA (xi) SEQUENCE DESCRIPTION: SEQ ID NO:4:

AAACTCCTGG AAATCAGTA                                                  19

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:5:

GCGTGATATA CTACTCCCTG T                                               21

(2) INFORMATION FOR SEQ ID NO:6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:6:

GCTGATAATG AAAGTGTG                                                   18

(2) INFORMATION FOR SEQ ID NO:7:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

CATGTGGATA TTTTGCA                                                    17

(2) INFORMATION FOR SEQ ID NO:8:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

AAACTCCTGG AAGTTAAAG                                                  19

(2) INFORMATION FOR SEQ ID NO:9:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

AAATAACGGT GTGGGAAAA                                                                 19

DETECTION OF PROTOZOAN PARASITES

TECHNICAL FIELD

The invention relates to detection of protozoan parasites, particularly Neospora and Toxoplasma species using polymerase chain reaction (PCR) techniques and in particular to the detection of *Neospora caninum* and *Toxoplasma gondii* in clinical and veterinary samples.

BACKGROUND OF THE INVENTION

*Neospora caninum* and *Toxoplasma gondii* are closely related protozoan parasites responsible for disease in a wide range of animals. *N. caninum* has recently been recognised as an important cause of neuromuscular disease in dogs, and as a cause of abortion and neonatal mortality in cattle and other domestic animals. *T. gondii* is a common cause of ovine abortion, and is one of the most important opportunistic pathogens in immunosuppressed human patients, such as those with acquired immune deficiency syndrome. Effective management of neosporosis and toxoplasmosis requires prompt diagnosis and treatment. The development of a range of efficient diagnostic tests is therefore essential.

Diagnosis of neosporosis and toxoplasmosis is difficult due to the vague nature of early clinical signs and the low numbers of parasites present in infected tissues. In the past, neosporosis was misdiagnosed as toxoplasmosis because of the similarities in clinical signs and pathological changes associated with infection with each organism. While serological and immunohistochemical techniques may aid diagnosis, clinically normal animals may have antibody titres suggestive of disease, and interpretation of immunohistochemistry is sometimes difficult due to variable staining and cross-reactivity. Molecular biological techniques such as the polymerase chain reaction (PCR) offer a highly sensitive and specific alternative to immunologic approaches to diagnosis. Previously developed PCR protocols for *N. caninum* and *T. gondii*, however, have not fully exploited the potential of this technique.

The PCR protocols developed by the present inventors utilize primers which hybridise within the internal transcribed saucer 1 (ITS1) region of the ribosomal RNA (rRNA) gene Unit of *N. caninum* and *T. gondii* (Payne and Ellis, 1990). The ITS1 region of the rRNA gene unit is relatively variable but also contains conserved regions consistent with its role in processing the rRNA molecule. Both the ribosomal RNA and the transcribed spacer regions have significant secondary structure due to their rule in protein translation and in the processing of the rRNA molecules respectively.

In the absence of a species-specific gene, the ITS1 region maybe a target for diagnostic PCR, as it is present at high copy number and exhibits high inter-species variability, while being generally conserved within a species Payne and Ellis, 1996). Furthermore, the ITS1 is readily sequenced and characterized because it is flanked by the 18S and 5.8S rRNA genes. The ITS1 regions of *N. caninum* and *T. gondii* are 421 and 392 bp, respectively, and the similarity between the two species is 82% (Payne and Ellis, 1996). Guay and co-workers (1993) estimated there to be around 110 copies of the ribosomal RNA gene unit in each *T. gondii* genome.

High sensitivities have been reported for PCR protocols targeting the ribosomal RNA gene unit, due to the high gene copy number. Guay and co-workers (1993) described a PCR capable of detecting a single organism using primers specific for the ITS1 region of *T. gondii*. Holmdahl and Mattson (1995) and Payne and Ellis (1996) recently remand PCR protocols for the detection of *N. caninum* with was capable of detecting five and seven organisms respectively. While these tests were specific for *N. caninum*, the sensitivity of the techniques is inadequate for diagnostic PCR because organisms may be present in tissues only in very low numbers and target DNA in some clinical samples may be degraded.

The present inventors have developed a sensitive PCR test for protozoan parasites that is particularly suitable for use in the detection of these microorganisms in clinical and biological samples.

SUMMARY OF THE INVENTION

In a first aspect, the present invention consists in a method of detecting a protozoan parasite in a sample containing the parasite, the method comprising the steps of:

(a) adding to the sample a pair of flanking oligonucleotide primers, at least one flanking primer being specific for and each being complementary to an opposite strand of a double stranded DNA molecule encoding the ITS1 of the protozoan parasite and flanking a region of the ITS1;

(b) further adding to the sample a pair of nested oligonucleotide primers, each nested primer being specific for and complementary to an opposite strand of the DNA encoding the ITS1 of the protozoan parasite, the nested primers being complementary to the region of the ITS1 spanned by the flanking primers;

(c) providing buffers, reagents, nucleotides and a thermostable DNA polymerase to the sample to form a reaction mixture;

(d) heating the sample to a temperature such that the double stranded DNA encoding the ITS1 of the protozoan parasite denatures to form single stranded DNA molecules;

(e) cooling the denatured sample to a temperature such that only the flanking primers anneal to their respective complementary sequences on the denatured DNA molecules;

(f) heating the denatured and annealed sample to a temperature such that the DNA polymerase extends the primers to form new double stranded DNA molecules spanning the region of the ITS1 defined by the flanking primers;

(g) repeating steps (d), (e) and (f) such that the number of copies of the region of DNA encoding the ITS1 region is amplified;

(h) heating the sample to a temperature such that the newly amplified double stranded DNA encoding the ITS1 region denatures to form single stranded DNA molecules;

(i) cooling the denatured sample to a temperature such that only the nested primers anneal to their respective complementary sequences on the denatured DNA;

(j) heating the denatured and annealed sample to a temperature such that the DNA polymerase extends the primers to form new double stranded DNA molecules spanning the region of the ITS1 defined by the nested primers;

(k) repeating steps (h), (i) and (j)) such that the number of copies of the region of DNA is amplified; and (l) detecting the amplified DNA.

The sample can be any sample including fixed or frozen tissue samples, and any biological fluid including semen, sputum, blood, saliva, cerebrospinal spinal fluid, cord blood and other excretion. Usually the sample is pre-treated to extract or concentrate the nucleic acid material from the sample by standard methods known to the art. Preferably, the method is carried out in one reaction vessel.

In a preferred embodiment of the present invention the protozoan parasite is a Neospora spp or a Toxoplasma spp. More preferably the Neospora spp is *N. caninum* and the Toxoplasma spp is *T. gondii*.

Preferably, in the method for detection of *N. caninum* the flanking oligonucleotide primers include SEQ ID NO:5 (forward) and SEQ ID NO:9 (reverse) and the nested oligonucleotide primers include SEQ ID NO:6 or SEQ ID NO:7 (forward) and SEQ ID NO:8 (reverse) or portions thereof. More preferably the primers are SEQ ID NO:5, SEQ ID NO:9, SEQ ID NO:6 or SEQ ID NO;7 and SEQ ID NO:8. Preferably, in the method for detection of *T. gondii* the flanking oligonucleotide primers include SEQ ID NO:1 (forward) and SEQ ID NO:9 (reverse) and the nested oligonucleotide primers include SEQ ID NO:3 (forward) and SEQ ID NO:4 (reverse) or portions thereof. More preferably the primers are SEQ ID NO:1, SEQ ID NO:9, SEQ ID NO:3 and a SEQ ID NO:4. It will be appreciated that the primers can be longer (or shorter) by the addition (or removal) of one or more bases at both or either ends.

In a preferred form of the present invention, one of the flanking primers is designed from an ITS1 sequence common to Neospora and Toxoplasma species and the other flanking primer is designed from an ITS1 sequence specific to the parasite to be detected. Most preferably, the primer common to Neospora and Toxoplasma species is the reverse primer SEQ ID NO:9.

The preferred primers for use in the present invention are defined below:

SEQ ID NO.1 CATTCACAGTCCTTATTCTTTA (TF1)
SEQ ID NO:2 CGCTGCTTCCAATATTG (TS3)
SEQ ID NO:3 TCCATTGGAGAGATTTG (TS4)
SEQ ID NO:4 AAACTCCTGGAAATCAGTA (TR1)
SEQ ID NO:5 GCGTGATATACTACTCCCTGT (NF1)
SEQ ID NO:6 GCTGATAATGAAAGTGTG (NS1)
SEQ ID NO:7 CATGTGGATATTTTGCA (NS2)
SEQ ID NO:8 AAACTCCTGGAAGTTAAAG (NR1)
SEQ ID NO:9 AAATAACGGTGTGGGAAAA (SR1)

In order to assist in the performance of the present invention, a higher concentration of nested primers is used compared to the concentration of flanking primers. A ratio of 100 to 1 of nested primers verses flanking primers is preferably used so that both sets of primers can be added in step (c). Alternatively, the nested primers are added after the initial amplification in step (g).

The flanking and nested oligonucleotide primers define the region of the ITS1 of the protozoan parasite that is suitable for the present method and gives the method its specificity for the parasite to be detected. It will be appreciated that any nested primers that are specific for the DNA region defined by the flanking primers would be suitable. For the method to function correctly, the nested primers should have lower melting points from those of the flanking primers. This difference in melting points ensures that during step (g) only the newly amplified DNA from step (f) is amplified via the flanking primers.

The present inventors have found that a further reduction in the denaturation temperature after initial amplification prevents dissociation of the external product, resulting in selective annealing and extension of the nested primers in the later stages of amplification. Low concentrations of flanking primers and late entry of the nested primers into the amplification reaction may assist in the delay of formation of non-specific amplification products, allowing an increased number of thermal cycles and thus enhanced sensitivity. Amplification specificity is also enhanced, as any non-target sequences amplified by the flanking primers are extremely unlikely to support further amplification by the nested primers.

The reagents used in step (c) are standard reagents commonly used in PCR and are used at known concentrations. Preferably the DNA polymerase is Taq DNA polymerase.

The detection of the amplified DNA in step (l) can be by any means known to the art. Preferably, the DNA is detected by electrophoresis.

In a most preferred embodiment of the method to detect *N. caninum* using the flanking primers SEQ ID NO:5 (forward) SEQ ID NO:9 (reverse) and the nested primers are SEQ ID NO:7 (forward) and SEQ ID NO:8 (reverse), the temperatures and cycling times are as follows:

(g) 5 cycles of 94° C. for 30 seconds, 60° C. for 150 seconds, 72° C. for 30 seconds;

(g) 15 cycles of 88° C. for 30 seconds, 60° C. for 30 seconds, 72° C. for 30 seconds;

(k) 10 cycles of 88° C. for 30 seconds, 54° C. for 30 seconds, 72 °C. for 30 seconds;

(k) 20 cycles of 86° C. for 30 seconds, 54° C. for 30 seconds, 72° C. for 30 seconds.

In a most preferred embodiment of the method to detect *T. gondii* using the flanking primers SEQ ID NO:1 (forward) SEQ ID NO:9 (reverse) and the nested primers are SEQ ID NO:3 (forward) and SEQ ID NO:4 (reverse), the temperatures and cycling times are as follows:

(g) 5 cycles of 94° C. for 30 seconds, 60° C. for 150 seconds, 72° C. for 30 seconds;

(g) 15 cycles of 88° C. for 30 seconds, 60° C. for 30 seconds, 72° C. for 30 seconds;

(k) 10 cycles of 88° C. for 30 seconds, 54° C. for 30 seconds, 72° C. for 30 seconds;

(k) 20 cycles of 86° C. for 30 seconds, 54° C. for 30 seconds, 72° C. for 30 seconds.

The present inventors enhanced the sensitivity of a diagnostic PCR by subjecting the product of an initial PCR reaction to further amplification using internal, or "nested primers". Nested amplification was achieved in a single tube using "drop-in, drop-out" nested primers and a thermal profile which selectively extended the flanking primer pair, then the nested primer pair.

The optimised single tube nested PCR test of the present invention is sensitive to a single copy of target sequence and specific for the target microorgmaism. Its diagnostic utility was assessed using formalin-fixed tissues from dogs suspected of having neosporosis or toxoplasmosis.

In a second aspect, the present invention consists in the oligonucleotide primers SEQ ID NO:5, SEQ ID NO:6, SEQ ID NO:7, SEQ ID NO:8, SEQ ID NO:1, SEQ ID NO:2, SEQ ID NO:3, SEQ ID NO:4 and SEQ ID NO:9.

In a third aspect, the present invention consists in a method of amplifying *Neospora caninum* DNA by polymerase chain reaction (PCR) using a pair of oligonucleotide primers, one oligonucleotide primer being specific for and complimentary to the ITS1 of *N. caninum*, and the other primer being complimentary to an ITS1 sequence common to Neospora and Toxoplasma species.

Preferably, one primer includes the sequence SEQ ID NO:6 or SEQ ID NO:7 or portions thereof, and the other primer includes the sequence SEQ ID NO:9 or portion thereof. More preferably, the primers are SEQ ID NO:6 or SEQ ID NO:7 and SEQ ID NO:9 and the amplification utilises standard PCR methods. The method according to the third aspect of the present invention can be used to detect the presence of N. caninum in a sample by detecting the presence of the DNA amplified by the PCR test using the primers of the invention.

The amplified DNA product using the primers SEQ ID NO:6 and SEQ ID NO:9 comprises approximately 137 bp and the amplified DNA product using the primers SEQ ID NO:7 and SEQ ID NO:9 comprises approximately 182 bp. The amplified DNA products can be detected by standard methods known to the art.

In a fourth aspect, the present invention consists in a method of amplifying Toxoplasma gondii DNA by polymerase chain reaction (PCR) using a pair of oligonucleotide primers, one oligonucleotide primer being specific for and complimentary to the ITS1 of T. gondii, and the other primer being complimentary to an ITS1 sequence common to Neospora and Toxoplasma species.

Preferably, one primer includes the sequence SEQ ID NO:2 or SEQ ID NO:3 or portions thereof, and the other primer includes the sequence SEQ ID NO:9 or portion thereof. More preferably, the primers are SEQ ID NO:2 or SEQ ID NO:3 and SEQ ID NO:9 and the amplification utilises standard PCR methods. The method according to the fourth aspect of the present invention can be used to detect the presence of T. gondii in a sample by detecting the presence of the DNA amplified by the PCR test using the primers of the invention.

The amplified DNA product using the primers SEQ ID NO:2 and SEQ ID NO:9 comprises approximately 144 bp and the amplified DNA product using the primers SEQ ID NO:3 and SEQ ID NO:9 comprises approximately 221 bp. The amplified DNA products can be detected by standard methods known to the art.

It was found that the methods according to the third and fourth aspects of the present invention were not sensitive to detect the presence of low numbers of Neospora spp and Toxoplasma spp respectively, in biological samples including frozen and fixed tissue samples. The method according to the first aspect of the present invention was then developed by the present inventors and had the surprising advantage at being able to detect low numbers of organisms in such biological samples.

In order that the present invention may be more clearly understood preferred forms will be described with reference to the following examples and drawings.

DETAILED DESCRIPTION OF THE INVENTION

1. MATERIALS AND METHODS 1.1 DNA samples

Parasite genomic DNA used in the PCR was phenol chloroform extracted from cell culture-derived tachyzoites of N. caninum and T. gondii. Canine and bovine genomic DNA/Dog and cow genomic DNA/Genomic DNA from dog and cow (Promega, USA) were used as host animals controls.

1.2 Tissue sections

Formalin-fixed, paraffin embedded brain tissue sections from a dog and an aborted bovine foetus with naturally acquired neosporosis, and a dog with naturally acquired toxoplasmosis (all confirmed by immunohistochemistry and IFAT) were used as positive controls. Tissue sections from a dog and cow with no clinical signs of protozoal disease (which tested negative for both Neospora and T. gondii IFAT and immunohistochemistry) were used as negative controls.

Tissues from 10 dogs with clinical signs suggestive of neosporosis or toxoplasmosis were tested by PCR in parallel with immunohistochemistry. Sections from the brain and muscle of 10 healthy dogs were used as normal controls.

1.3 Reaction setup

All manipulations for PCR were performed in a Class II Biological Safety Cabinet dedicated to PCR. The precautions against contamination recommended by Dragon and co-workers (1994) were implemented. Amplifications were performed in 600 µl microfuge tubes (Trace Biosciences, Australia).

For each experiment, reagents for all reactions were prepared as a master mix containing all reagents except template DNA, to minimise labour, operator error and artefactual variation between reactions in optimisation experiments. Reagents were kept chilled on ice at all times, and one reagent (such as dNTPs or magnesium) was withheld until immediately before the master mix was added to sample DNA to minimise template independent polymerase activity. The reactions were overlaid with mineral oil to prevent evaporation, the tubes were capped and placed immediately in a thermal cycler (Hybaid Omnigene® thermal cycler, Hybaid, USA) preheated to 95° C. The thermal cycler program was then commenced.

Following thermal cycle, amplification products were refrigerated until electrophoretic analysis on 2% agarose gels.

1.4 Conventional PCR

Figure 1:
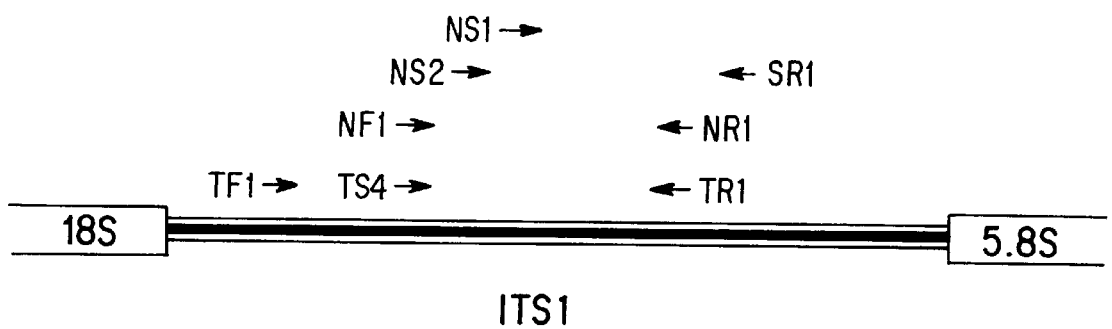
FIG. 1 shows the relative positions of PCR primers within the ITS1 region of N. caninum and T. gondii.
Figure 2:
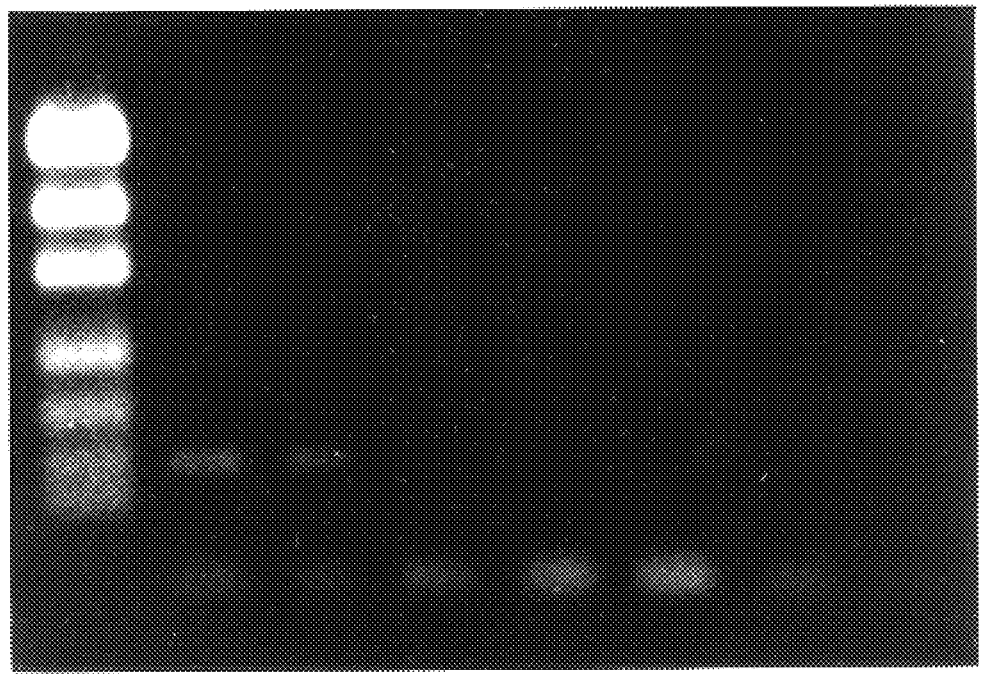
FIG. 2 is electrophoresis analysis showing specificity of N. caninum single tube nested PCR, Lane 1 N. caninum (NC-Liverpool isolate) DNA; Lane 2 N. caninum (NC-1 isolate) DNA; Lane 3 T. gondii (RH strain) DNA; Lane 4 T. gondii (ME-49) DNA: Lane 5 Sarcocystis cruzi DNA; Lane 6 Dog DNA; and Lane 7 Cow DNA.
Figure 3:
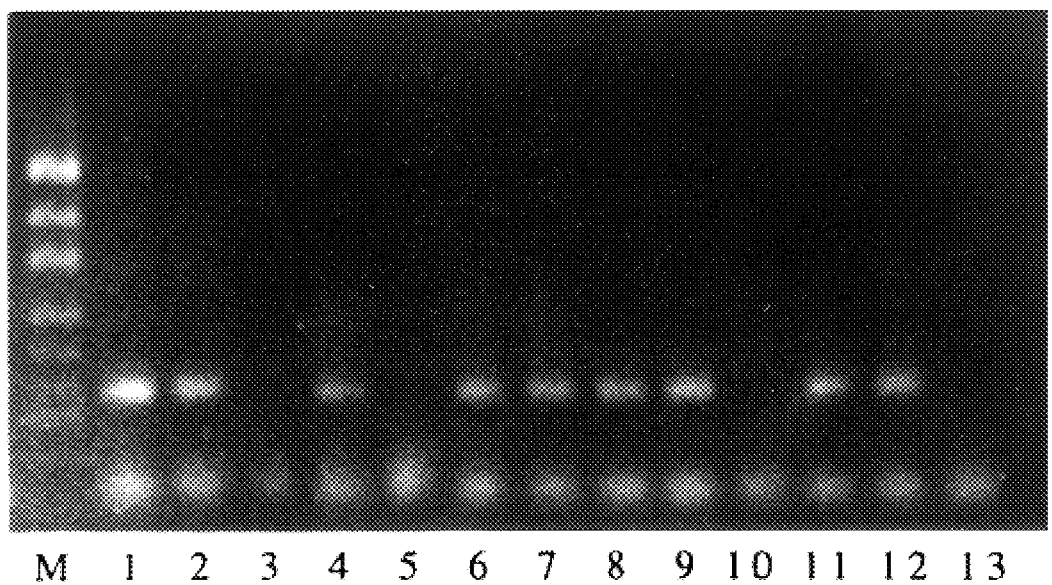
FIG. 3 is electrophoresis analysis showing specificity of optimised N. caninum single tube nested PCR, Lane 1 100 fg N. caninum DNA; Lane 2 10 fg; Lane 3 1 fg; lane 4 reagent control (no DNA)
Figure 4:
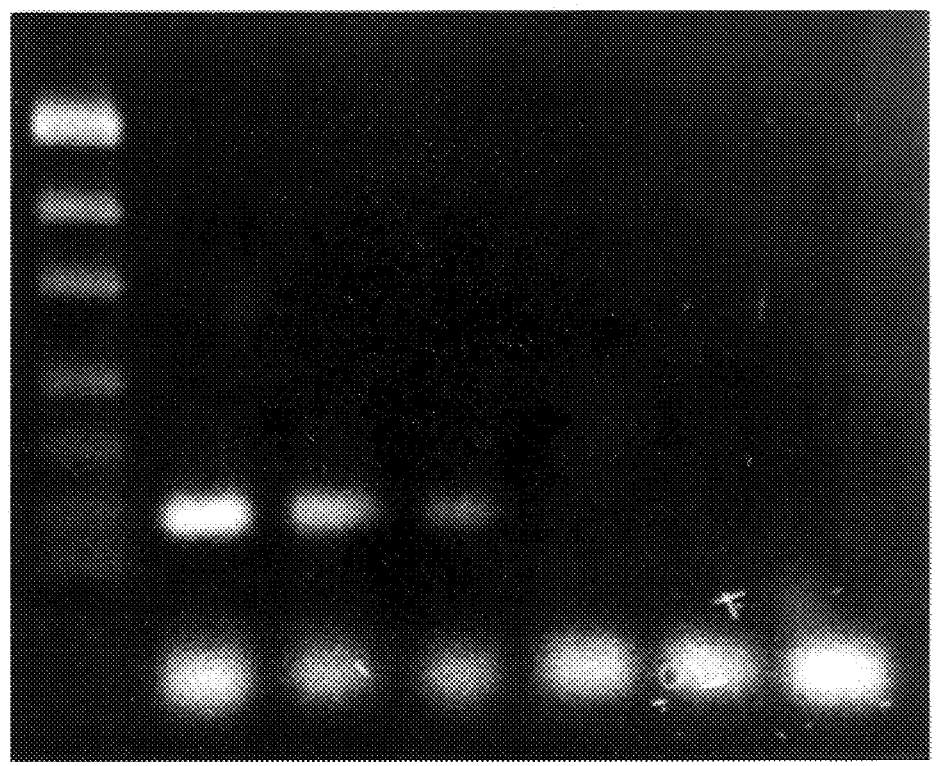
FIG. 4 shows amplification of N. caninum DNA from formalin-fixed, paraffin embedded tissue sections Lane 1, Negative control dog brain tissue+10 fg parasite N. caninum DNA; Lane 2, Brain tissue from dog infected with N. caninum; Lane 3, Brain tissue from aborted bovine foetus infected with Neospora spp; Lane 4, Brain tissue from dog infected with T. gondii, Lane 5, Negative control dog brain tissue section; Lane 6, Negative control brain cow issue section.
Figure 5:
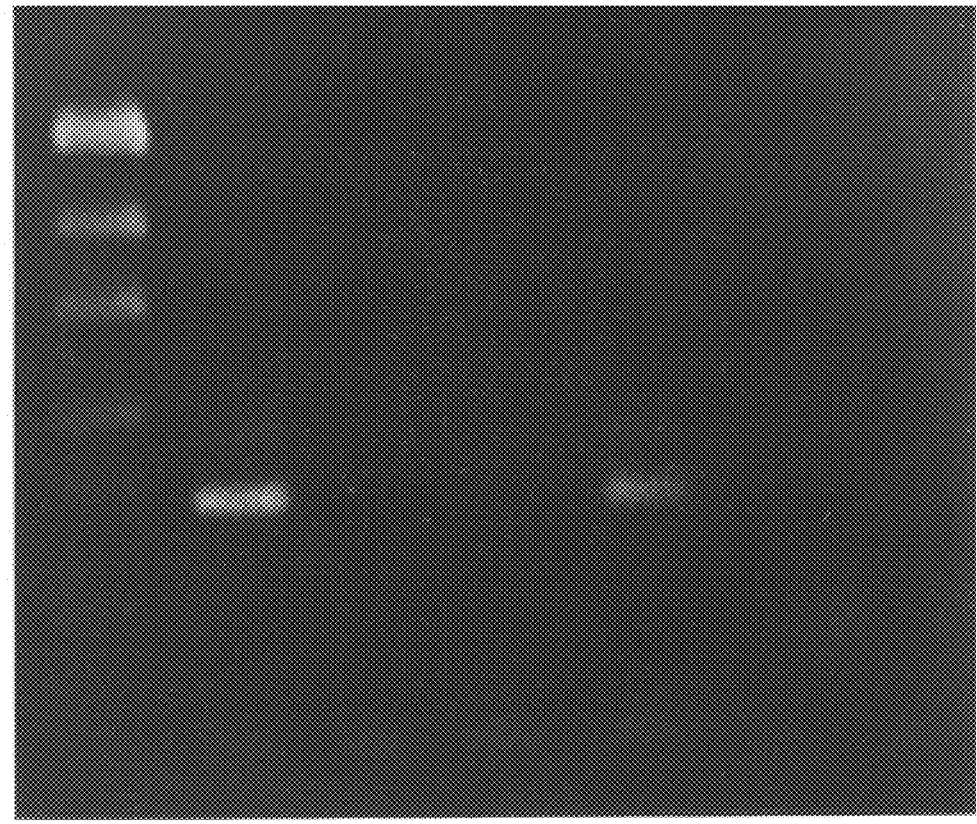
FIG. 5 shows amplification of T. gondii DNA from formalin-fixed, paraffin embedded tissue sections. Lane 1, Negative control dog brain tissue+10 fg T. gondii DNA; Lane 2, Brain tissue from dog infected with N. caninum; Lane 3, Brain tissue from aborted bovine foetus infected with Neospora spp; Lane 4, Brain tissue from dog infected with T. gondii, Lane 5, Negative control dog brain tissue section; Lane 6, Negative control brain cow tissue section.

The conventional 30 cycle PCR protocol developed in the inventors' laboratory utilised a forward primer specific for either N. caninum or T. gondii and a conserved reverse primer (SEQ ID NO:6, SEQ ID NO:2 or SEQ ID NO:3 and SEQ ID NO:9 respectively, see Table 1, FIG. 1). This protocol was used as a starting point in determining optimal reaction conditions for each new primer pair. Reaction conditions were as follows 1xPCR Buffer/0.2 mM each dNTP/50 µM each primer/0.5 units of Taq DNA polymerase in a total reaction volume of 50 μl. Tubes were overlaid with mineral oil and placed in a Hybaid Omnigene thermal cycler programmed for 95° C. for 5 minutes; 30 cycles of 94° C. for 30 seconds, 55° C. for 30 seconds, 72° C. for 30 seconds; and finally 72° C. for 10 minutes.

TABLE 1

| Primer ID NO | Sequence (5'–3') | Specificity | Direction | Position | Melting Point (0° C.) |
|---|---|---|---|---|---|
| 1 | CATTCACAGTCCTTATTCTTTA | T. gondii | Forward | External | 56.1 |
| 2 | CGCTGCTTCCAATATTG | T. gondii | Forward | | |
| 3 | TCCATTGGAGAGATTTG | T. gondii | Forward | Nested | 49.4 |
| 4 | AAACTCCTGGAAATCAGTA | T. gondii | Reverse | Nested | 49.5 |
| 5 | GCGTGATATACTACTCCCTGT | N. caninum | Forward | External | 56.5 |
| 6 | GCTGATAATGAAAGTGTG | N. caninum | Forward | Nested | 48.0 |
| 7 | CATGTGGATATTTTGCA | N. caninum | Forward | Nested | 48.6 |
| 8 | AAACTCCTGGAAGTTAAAG | N. caninum | Reverse | External | 48.6 |
| 9 | AAATAACGGTGTGGGAAAA | conserved | Reverse | External | 55.5 |

1.5 Single tube nested PCR

For single tube nested PCR, a new flanking forward and nested reverse primer specific for each N. caninum and T. gondii were designed to complement existing primers (see Table 1 and FIG. 1). As DNA in some clinical samples may be degraded due to aging or chemical fixation, flanking primers were selected so as to amplify as short a fragment as practical.

The flanking primers were designed so as to have a similar melting point to SEQ ID NO:9, and the nested primers a lower melting point, closer to that of SEQ ID NO:6 or SEQ ID NO:3. The optimal annealing temperature of each primer pair (taken as the highest annealing temperature which resulted in undiminished reaction yield) was determined in a 30 cycle conventional PCR using 25 ng of genomic DNA. At this point, SEQ ID NO:6 was replaced with another N. caninum-specific primer, SEQ ID NO:7, to overcome excessive amplification artefact formation encountered using SEQ ID NO:6, SEQ ID NO:8 and SEQ ID NO:5 together.

Reaction conditions for single tube nested PCR using the four primers were optimised using a 55 cycle PCR and 100 fg of genomic DNA. Starting conditions were identical to those used in conventional PCR, except the nested and flanking primers were present at concentrations of 50 μM and 2 μM respectively. Because of the large number of reaction variables important in single tube nested PCR (including reagent concentrations, cycle parameters and setup conditions), screening experiments were conducted to determine the parameters which could be modified to enhance amplification sensitivity and specificity. Primer concentrations, initial cycle parameters, hot start protocols and amount of sample (for tissue section extracts) were further optimised using a 55 cycle, 10 fg genomic DNA amplification to optimise the PCR for low copy number amplifications. To investigate any potential inhibitory effect of substances present in tissue sections, amplifications using 1, 10, 20 or 30 μl of negative control tissue section and 10 fg of genomic DNA were performed. Tissue sections through blood vessels containing approximately 30% blood cells (by area) were also tested, as compounds present in blood may inhibit PCR.

1.6 Specificity of optimised protocol

The specificity of the optimised single tube nested PCR protocols were evaluated by test 1 ng of genomic DNA from each N. caninum (NC-1 and NC-Liverpool isolates), T. gondii (RH- and ME49 strains), Sarcocystis cruzi, dog and cow.

1.7 Sensitivity of optimised protocol

The sensitivity of the optimised protocols were evaluated using serial tenfold dilutions of genomic DNA of either N. caninum or T. gondii genomic DNA. 10 replicates of 1 fg were tested.

1.8 Formalin-fixed, paraffin-embedded tissue sections

To investigate the utility of the optimised PCRs with clinical materials, Neospora-positive tissue sections from the brain of a dog and an aborted bovine foetus, a T. gondii-positive section from a dog, and negative control sections from a dog and a cow were tested by PCR. Tissue sections were prepared in a separate building from where PCR was performed to prevent false positive results due to contamination with amplification products. Each 5 μm tissue section was placed in a 600 μl microfuge tube with 300 μl of sterile distilled water, overlaid with 50 μl of mineral oil, and heated on a thermal cycler for 15 min at 99.9° C. The tube was allowed to cool to room temperature, and 5 μl of solution tested using each the N. caninum and T. gondii PCR. Immunohistochemistry using hyperimmune goat sera raised against N. caninum or T. gondii (VMRD, USA) and an avidin biotin peroxidase complex (Dako, Australia) was used in parallel with PCR as an indicator of true status.

2 RESULTS 2.1 Optimised single tube nested PCR protocol

Optimal conditions for both N. caninum and T. gondii were very similar. The final reaction conditions were 5 μl of test sample/1xPCR Buffer/0.2 mM each dNTP/50 μM each nested primer/0.5 μM each flanking primer/0.8 units of Taq DNA polymerase in a total reaction volume of 50 μl. The thermal cycler was programmed as follows: 95° C. for 5 minutes;

5 cycles of 94° C. for 30 seconds, 60° C. for 150 seconds, 72° C. for 30 seconds;

15 cycles of 88° C. for 30 seconds, 60° C. for 30 seconds, 72° C. for 30 seconds;

10 cycles of 88° C. for 30 seconds, 54° C. for 30 seconds, 72 °C. for 30 seconds;

20 cycles of 86° C. for 30 seconds, 54° C. for 30 seconds, 72° C. for 30 seconds; and finally 72° C. for 10 minutes.

Reaction setup was found to be extremely important in maximising the sensitivity of the PCR. Reactions promptly set up and placed in the thermal cycler were 10- to 100-fold more sensitive than reactions allowed to sit for several minutes at room temperature. "Hot start PCR" using ampliwax PCR gems (Perkin Elmer Cetas) did not further improve sensitivity.

Inhibition of amplification by tissue sections was not observed, even when up to 60% of the reaction volume was composed of boiled tissue section, or when tissue sections containing blood were used (data not shown).

2.2 Specificity of optimised protocol

The *N. caninum* single tube nested PCR amplified the predicted 146 bp product from both the NC-1 and NC-Liverpool isolates of *N. caninum*, but not from dog, cow, or either *T gondii* strain tested. The *T. gondii* single tube nested PCR amplified the predicted 183 bp product from both the RH and ME-49 strains of *T. gondii*, but not from the host animal controls or from either *N. caninum* isolate.

2.3 Sensitivity of optimised protocol

The *N. caninum* single tube nested PCR amplified the predicted 146 bp product from the 100 fg, 10 fg and two of five 1 fg *N. caninum* genomic DNA amplification reactions.

2.4 Formalin-fixed, paraffin-embedded tissue sections

The *N. caninum* single tube nested PCR amplified the predicted 146 bp product from a normal dog tissue section spiked with *N. caninum* genomic DNA. a Neospora-infected dog and Neospora-infected aborted bovine foetal brain sections, but not from the *T. gondii* infected dog brain, the normal dog brain or normal cow brain tissue sections. The *T. gondii* protocol amplified the predicted 183 bp product from a normal dog tissue section spiked with 10 fg of genomic DNA and from a *T. gondii*-infected dog brain section, but not from normal dog or cow brain sections, nor from the Neospora-infected dog or cow brain sections.

2.5 Comparative efficiency of immunohistochemistry and PCR diagnosis from tissue sections To investigate the utility of the optimised PCRs with clinical materials, Neospora-positive tissue sections from the brain of a dog and an aborted bovine foetus, a *T. gondii*-positive section from a dog, and negative control sections from a dog and a cow were tested by PCR. Tissue sections were prepared in a separate building from where PCR was performed to prevent false positive results due to contamination with amplification products. Each 5 μm tissue section was placed in a 600 μl microfuge tube with 300 μl of sterile distilled water, overlaid with 50 μl of mineral oil, and heated on a thermal cycler for 15 min at 99.9° C. The tube was allowed to cool to room temperature, and 5 μl of solution tested using each the *N. caninum* and *T. gondii* PCR. Immunohistochemistry using hyperimmune goat sera raised against *N. caninum* or *T. gondii* (VMRD, USA) and an Avidin biotin peroxidase complex (Dako, Australia) was used in parallel with PCR as an indicator of true status. The results of *N. caninum* and *T. gondii*-specific PCR and immunohistochemistry are shown in Table 2.

TABLE 2

Results of histopathological, immunohistochemical examination and PCR testing of tissue sections from 10 dogs with clinical signs suggestive of neosporosis or toxoplasmosis.

| Dog | Brain Lesions | Brain PCR | IHC | Le- sions | Muscle PCR | IHC | Diagnosis |
|---|---|---|---|---|---|---|---|
| 1 | + | – | T | + | – | T | toxoplasmosis (t) |
| 2 | – | – | – | + | N | N | neosporosis (n) |
| 3 | + | N | N | + | N | N | neosporosis |
| 4 | + | N,T | N,T | + | N,T | N,T | both n and t |
| 5 | + | – | – | + | N | N | neosporosis |
| 6 | + | – | – | + | N | N | neosporosis |
| 7 | + | – | – | + | – | – | unknown |
| 8 | + | N | N | + | – | – | neosporosis |
| 9 | + | N | N | + | N | N | neosporosis |
| 10 | + | N | N | + | – | – | neosporosis |

N = *N. caninum*; T = *T. gondii*; + = present; – = absent

Brain and muscle tissues from 10 dogs with clinical signs suggestive of neosporosis or toxoplasmosis were tested using both the optimised single tube nested PCR and immunohistochemistry. Sections from the brain and muscle of 10 healthy dogs were used as normal controls. Three sections from both brain and muscle tissue were tested using each *N. caninum* and *T. gondii*-specific immunohistochemistry and PCR. One section from each tissue was stained with haematoxylin and eosin (H&E) for routine histopathological examination. Table 2 represents each tissue classified by the presence or absence of pathological changes suggestive of protozoal disease, and by the immunohistochemistry and PCR results. None of the normal control dogs tested positive for either *N. caninum* or *T. gondii* by either technique. In the tissues from the clinic dogs, organisms were sometimes detected in only a proportion of the sections examined from a tissue, though pathological changes were typically observed in each section examined. One of the clinic dogs tested positive for *T. gondii* only, seven dogs tested positive for *N. caninum* only, and one dog (#4) tested positive for both organisms. One dog (#7) tested negative for both organisms, despite having lesions in each tissue.

While PCR has been applied to the detection of a number of protozoa, including *N. caninum* and *T. gondii*, previously reported PCR protocols for these organisms have not exploited the potential sensitivity of this technique. The present inventors employed a second, nested amplification in a single tube to enhance the sensitivity and specificity of PCR protocols for the detection of *N. caninum* and *T. gondii*. The optimised single tube nested PCR was able to detect as little as 1 fg of genomic DNA, representing an improvement in sensitivity of around 700 times that of the conventional PCR protocol. The results observed with the 1 fg replicates are consistent with a Poisson distribution, suggesting the assay is capable of detect the presence or absence of a single copy of target sequence. Hence, performing nested amplifications in a single tube was effective in enhancing the sensitivity of a PCR for the detection of *N. caninum* or *T. gondii*. Successful amplification of parasite DNA from formalin-fixed, paraffin embedded tissue sections confirmed the suitability of the assay for testing clinical material from naturally infected animals. The single tube nested PCR was as sensitive as immunohistochemistry in detecting *N. caninum* infections in formalin-fixed, paraffin-embedded tissue sections.

In conventional PCR the number of cycles which can be profitably performed is limited by the formation of primer-dependant amplification artefacts (such as "primer dimers"). In singe-tube nested PCR, primers are designed such that flanking primers have a higher melting point than nested primers (by virtue of greater length or G+C content). A thermal profile is then employed which first allows selective annealing and extension of external but not nested primers. The annealing temperature then reduced, enabling annealing of the nested primers and amplification of the nested product from the initial product. A further reduction in the denaturation temperature prevents dissociation of the external product, resulting in selective annealing and extension of the nested primers in the later stages of amplification. Low concentrations of flanking primers and late entry of the nested primers into the amplification reaction delay the formation of nonspecific amplification products, allowing an increased number of thermal cycles and thus enhanced sensitivity. Amplification specificity is also enhanced, as any non-target sequences amplified by the flanking primers are extremely unlikely to support further amplification by the nested primers.

The optimised protocol according to the present invention incorporated several strategies to maximise amplification sensitivity and specificity. To minimise non-specific priming prior to the reactions reaching the denaturation temperature, preferably reagents and samples were kept chilled on ice, and reactions were promptly assembled and placed into a preheated thermal cycler. The denaturation temperature was reduced from 94° C. to 87° C. after the first five rounds to minimise spurious product formation and amplification inhibition associated with large amounts of non-specific DNA (this also reduced the duration of thermal cycling). An extended annealing time of 150 seconds was used for the first five cycles to ensure amplification of rare target sequences.

Had the single tube nested PCR protocol been developed de nova, flanking primers would have been designed longer than nested primers, to give an optimal annealing temperature close to 72° C., enhancing specificity and shorten thermal cycling time. The incorporation of a GC clamp (a tail of guanine and cytosine bases at the 5' end of flanking primers, which raises the denaturation temperature of the amplification product, allowing complete "drop out" of the flanking primer product with reduced denaturation temperature in the later cycles of amplification) might also have been considered. While the difference in annealing and denaturation temperatures for the nested and flanking primers and products in the present protocol is only small, the PCR is nonetheless robust and reliable.

To ensure amplification specificity, potential primers were selected from regions of consistent sequence intraspecific conservation and interspecific variation using alignments of the ITS1 region from NC-1 and NC-Liverpool isolates of *N. caninum* and RH, P and Sailie strains of *T. gondii* (Genbank accession numbers U16160. U16159, X75453, X75429 and X75430 respectively. Potential primers were selected from regions of consistent conservation. Amplification protocols for *N. caninum* and *T. gondii* were developed in parallel because of the difficulties in differentiating infections with these organisms clinically and with immunologic techniques. Furthermore, given the genetic similarity of these organisms, it was felt that *T. gondii* was the organism most likely to give false-positive results in the *N. caninum* PCR, and vice-versa. It was desirable that the *N. caninum*- and *T. gondii*-specific protocols utilise identical thermal cycle programs to allow both assays to be performed simultaneously on a single thermal cycler. The similarity of the two optimised PCR protocols is testimony to the sequence and structure conservation in the ITS1 region of these two organisms.

A suitable method of sample preparation for PCR is to lyse cells to release DNA into solution without damage or degradation of the DNA, and without introducing or co-purifying substances which may inhibit amplification. Furthermore, it should be simple and rapid where possible, to reduce processing time, labour and the risk of contamination. It has been found by the present inventors that simple boiling is sufficient preparation for amplification of parasite DNA from tissue sections and cerebrospinal fluid. Some samples, however, such as faeces, blood or solid tissues may warrant further treatment. Preparation of samples by boiling allowed results from a group of samples to be obtained within an 8 hour day.

While the examples of the present invention focussed on formalin-fixed, paraffin embedded tissue sections, the single tube nested PCR has also been used to amplify parasite DNA from cerebrospinal fluid, fresh, and ethanol-fixed tissues, and should be readily adapted for other types of clinical material. Formalin-fixed tissues were focussed upon because archival material was always available for testing, preparation was simple, and the presence of organisms could be readily verified using immunohistochemistry or routine histology. This tissue type was considered a suitably stringent test of the sensitivity of the assay, as formalin fixation results in loss and degradation of DNA. While flanking primers were selected so as to define as short an amplification product as practical, formalin-fixed tissues are inferior to fresh, frozen or ethanol-fixed tissues as PCR substrates. Tissues fixed with unbuffered formalin. Zenler's, Bouin's or B5 solutions aregenerally considered unacceptable samples for PCR.

Occasional false positive results (date to contamination of reactions with previously amplified DNA) encountered during the development of the assay were minimised by strict maintenance of aseptic technique and a clean to dirty flow of material, equipment and personnel. Test samples were prepared in a separate building from where PCR was performed, and PCR reactions were prepared in a separate area, and, where possible, prior to electrophoretic analysis of amplification products in both the daily and weekly routine. Despite these precautions, the exquisite sensitivity of the single tube nested PCR means that occasional false positive results are possible. Therefore several known negative samples and reagent controls were included in each diagnostic PCR run. While several chemical and enzymatic protocols for the prevention of carry over contamination have been described, these have been found to be of limited efficacy for short amplification products.

The single tube nested PCR of the present invention provides a complement or alternative to immunohistochemistry and routine histology in detecting organisms in biopsy and postmortem samples. Furthermore, the wide range of material amenable to PCR analysis allows diagnosis of infection and the detection of organisms from other clinical samples, such as blood product, cerebrospinal fluid, amniotic fluid, lung aspirates and semen will be possible, often with minimal sample preparation. With appropriate sample preparation and DNA purification protocols, the assay will be useful in detecting organisms in the environment, or the faecas of potential definitive hosts. The assay will be useful in the study of disease development, maintenance and progression of infections. Finally with appropriate sample preparation protocols, the assay will be useful in detecting organisms in the environment, or the faeces of potential definitive hosts. Hence the single tube nested PCR provides a powerful new tool in the study of *N. caninum* and *T. gondii*, and the diagnosis of infection in animals.

The results of this study demonstrated that single-tube nested PCR was a practical way of enhancing the sensitivity of the existing *N. caninum* and *T. gondii* ITS1 PCR protocols. The optimised assay was able to detect a single copy of target sequence, and was specific for the organism targeted. In addition, the assay was able to detect *N. caninum* and *T. gondii* microorganisms in formalin-fixed, paraffin-embedded tissue sections from naturally infected dogs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Holmdahl, O. J. M. & Mattsson, J. G. (1996) Rapid and sensitive identification of *Neospora caninum* by in vitro amplification of the internal transcribed spacer 1. Parasitology 112, 177–182.

Guay, J. M., Dubois. D., Morency, M. J., Gagnong, S., Mercier, J. & Levesque, R. C. (1993) Detection of the pathogenic parasite *Toxoplasma gondii* by specific amplification of ribosomal sequences using comultiplex polymerase chain action. Journal of Clinical Microbiology 31, 203–207.

Dragon, E. A., Spadoro, J. P. and Madej, R. (1994) Quality Control of Polymerase Chain Reaction. In: *Diagnostic Molecular Biology: Principles and Applications.* (Persing, D. H., Smith, T. F., Tenover, F. C. & White, T. J.) Pp.161–169. Washington: American Society for Microbiology.

Payne, S. & Ellis, J. (1996) Detection of *Neospora caninum* DNA by the Polymerase Chain Reaction. International Journal of Parasitology 26, 347–351.

---

We claim:

1. A method of detecting a protozoan parasite in a sample containing the parasite, the method comprising the steps of:
   (a) adding to the sample a pair of flanking oligonuleotide primers, at least one flanking primer being specific for and each being complementary to an opposite strand of a double stranded DNA molecule encoding the ITS1 of the protozoan parasite and flanking a region of the ITS1, wherein the flanking oligonucleotide primers include SEQ ID NO:5 (forward) and SEQ ID NO:9 (reverse);
   (b) further adding to the sample a pair of nested oligonucleotide primers, each nested primer being specific for and complementary to an opposite strand of the DNA encoding the ITS1 of the protozoan parasite, the nested primers being complementary to the region of the ITS1 spanned by the flanking primers, wherein the nested oligonucleotide primers include SEQ ID NO:6 or SEQ ID NO:7 (forward) and SEQ ID NO:8 (reverse);
   (c) providing buffers, reagents, nucleotides and a thermostable DNA polymerase to the sample to form a reaction mixture;
   (d) heating the sample to a temperature such that the double stranded DNA encoding the ITS1 of the protozoan parasite denatures to form single stranded DNA molecules;
   (e) cooling the denatured sample to a temperature such that only the flanking primers anneal to their respective complementary sequences on the denatured DNA molecules;
   (f) heating the denatured and annealed sample to a temperature such that the DNA polymerase extends the primers to form new double stranded DNA molecules spanning the region of the ITS1 defined by the flanking primers;
   (g) repeating steps (d), (e) and (f) such that the number of copies of the region of DNA encoding the ITS1 region is amplified;
   (h) heating the sample to a temperature such that the newly amplified double stranded DNA encoding the ITS1 region denatures to form single stranded DNA molecules;
   (i) cooling the denatured sample to a temperature such that only the nested primers anneal to their respective complementary sequences on the denatured DNA;
   (j) heating the denatured and annealed sample to a temperature such that the DNA polymerase extends the primers to form new double stranded DNA molecules spanning the region of the ITS1 defined by the nested primers;
   (k) repeating steps (h), (i) and (j) such that the number of copies of the region of DNA is amplified; and
   (l) detecting the amplified DNA.

2. The method according to claim 1 wherein the sample is selected from the group consisting of fixed or frozen tissue samples, biological fluids including semen, sputum, blood, saliva, cerebrospinal spinal fluid, cord blood, and bodily excretions.

3. The method according to claim 1 such that the sample is pre-treated to extract or concentrate the nucleic acid material from the sample.

4. The method according to claim 1 carried out in one reaction vessel.

5. The method according to claim 1 wherein the protozoan parasite is a Neospora spp.

6. The method according to claim 1 wherein the Neospora spp is *N. caninum*.

7. The method according to claim 1 for the detection of *N. caninum* wherein the flanking oligonucleotide primers include SEQ ID NO:5 (forward) and SEQ ID NO:9 (reverse) and the nested oligonucleotide primers include SEQ ID NO:6 or SEQ ID NO:7 (forward) and SEQ ID NO:8 (reverse) or portions thereof.

8. The method according to claim 1 wherein one of the flanking primers is designed from an ITS1 sequence common to Neospora and Toxoplasma species and the other flanking primer is designed from an ITS1 sequence specific to the parasite to be detected.

9. The method according to claim 8 wherein the primer common to Neospora and Toxoplasma species is the reverse primer SEQ ID NO:9.

10. The method according to claim 1 wherein a higher concentration of nested primers is used compared to the concentration of flanking primers.

11. The method according to claim 10 in which there is a ratio of 100 to 1 of nested primers verses flanking primers and both sets of primers are added in step (c).

12. The method according to claim 1 wherein the nested primers have lower melting points than the melting points of the flanking primers.

13. The method according to claim 1 wherein the DNA polymerase is Taq DNA polymerase.

14. The method according to claim 1 wherein the detection of the amplified DNA in step (l) is by electrophoresis.

15. The method according to claim 1 using the flanking primers SEQ ID NO:5 (forward) and SEQ ID NO:9 (reverse) and the nested primers SEQ ID NO:7 (forward) and SEQ ID NO:8 (reverse), wherein the temperatures and cycling times are:
   (g) 5 cycles of 94° C. for 30 seconds, 60° C. for 150 seconds, 72° C. for 30 second;
   (g) 15 cycles of 88° C. for 30 seconds, 60° C. for 30 seconds, 72° C. for 30 second;
   (k) 10 cycles of 88° C. for 30 seconds, 54° C. for 30 seconds, 72° C. for 30 second;
   (k) 20 cycles of 86° C. for 30 seconds, 54° C .for 30 seconds, 72° C. for 30 second.

16. Oligonucleotide primers selected from the group consisting of SEQ ID NO:5, SEQ ID NO:6, SEQ ID NO:7, SEQ ID NO:8, SEQ ID NO:1, SEQ ID NO:2, SEQ ID NO:3, SEQ ID NO:4 and SEQ ID NO:9.

17. A method of amplifying *Neospora caninum* DNA by polymerase chain reaction (PCR) using a pair of oligonucleotide primers, one oligonucleotide primer being specific for and complimentary to the ITS1 of *N. caninum*, and the other primer being complimentary to an ITS1 sequence common to Neospora and Toxoplasma species, wherein the one primer includes the sequence SEQ ID NO:6 or SEQ ID NO:7, and the other primer includes the sequence SEQ ID NO:9.

18. The method according to claim 17 wherein the primers are SEQ ID NO:6 or SEQ ID NO:7, and SEQ ID NO:9, and the amplification utilizes standard PCR methods.

19. The method according to claim 18 wherein the amplified DNA product using the primers SEQ ID NO:6 and SEQ ID NO:9 comprises approximately 137 bp and the amplified DNA product using the primers SEQ ID NO:7 and SEQ ID NO:9 comprises approximately 182 bp.

20. A method of detecting a protozoan parasite in a sample containing the parasite, the method comprising the steps of:
(a) adding to the sample a pair of flanking oligonucleotide primers, at least one flanking primer being specific for and being complementary to an opposite strand of a double stranded DNA molecule encoding the ITS1 of the protozoan parasite and flanking a region of the ITS1, wherein the flanking oligonucleotide primers include SEQ ID NO:1 (forward) and SEQ ID NO:9 (reverse);
(b) further adding to the sample a pair of nested oligonucleotide primers, each nested primer being specific for and complementary to an opposite strand of the DNA encoding the ITS1 of the protozoan parasite, the nested primers being complementary to the region of the ITS1 spanned by the flanking primers, wherein the nested oligonucleotide primers include SEQ ID NO:3 (forward) and SEQ ID NO:4 (reverse);
(c) providing buffers, reagents, nucleotides and a thermostable DNA polymerase to the sample to form a reaction mixture;
(d) heating the sample to a temperature such that the double stranded DNA encoding the ITS1 of the protozoan parasite denatures to form single stranded DNA molecules;
(e) cooling the denatured sample to a temperature such that only the flanking primers anneal to their respective complementary sequences on the denatured DNA molecules;
(f) heating the denatured and annealed sample to a temperature such that the DNA polymerase extends the primers to form new double stranded DNA molecules spanning the region of the ITS1 defined by the flanking primers;
(g) repeating steps (d), (e) and (f) such that the number of copies of the region of DNA encoding the ITS1 region is amplified;
(h) heating the sample to a temperature such that the newly amplified double stranded DNA encoding the ITS1 region denatures to form single stranded DNA molecules;
(i) cooling the denatured sample to a temperature such that only the nested primers anneal to their respective complementary sequences on the denatured DNA;
(j) heating the denatured and annealed sample to a temperature such that the DNA polymerase extends the primers to form new double stranded DNA molecules spanning the region of the ITS1 defined by the nested primers;
(k) repeating steps (h), (i) and (j) such that the number of copies of the region of DNA is amplified; and
(l) detecting the amplified DNA.

21. The method according to claim 20 wherein the sample is selected from the group consisting of fixed or frozen tissue samples, biological fluids including semen, sputum, blood, saliva, cerebrospinal spinal fluid, cord blood, and bodily excretions.

22. The method according to claim 20 such that the sample is pre-treated to extract or concentrate the nucleic acid material from the sample.

23. The method according to claim 20 carried out in one reaction vessel.

24. The method according to claim 20 wherein the protozoan parasite is a Toxoplasma spp.

25. The method according to claim 20 wherein the Toxoplasma spp. is *T. gondii*.

26. The method according to claim 20 wherein a higher concentration of nested primers is used compared to the concentration of flanking primers.

27. The method according to claim 26 in which there is a ratio of 100 to 1 of nested primers verses flanking primers and both sets of primers are added in step (c).

28. The method according to claim 20 wherein the nested primers have lower melting points than the melting points of the flanking primers.

29. The method according to claim 20 wherein the DNA polymerase is Taq DNA polymerase.

30. The method according to claim 20 wherein the detection of the amplified DNA in step (l) is by electrophoresis.

31. The method according to claim 20 for the detection of *T. gondii* wherein the flanking oligonucleotide primers include SEQ ID NO:1 (forward) and SEQ ID NO:9 (reverse) and the nested oligonucleotide primers include SEQ ID NO:3 (forward) and SEQ ID NO:4 (reverse).

32. The method according to claim 31 wherein the primers are SEQ ID NO:1, SEQ ID NO:9, SEQ ID NO:3 and SEQ ID NO:4.

33. The method according to claim 20 using the flanking primers SEQ ID NO:1 (forward) and SEQ ID NO:9 (reverse) and the nested primers SEQ ID NO:3 (forward) and SEQ ID NO:4 (reverse), wherein the temperatures and cycling times are:
(g) 5 cycles of 94° C. for 30 seconds, 60° C. for 150 seconds, 72° C. for 30 seconds;
(g) 15 cycles of 88° C. for 30 seconds, 60° C. for 30 seconds, 72° C. for 30 seconds;
(k) 10 cycles of 88° C. for 30 seconds, 54° C. for 30 seconds, 72° C. for 30 seconds;
(k) 20 cycles of 86° C. for 30 seconds, 54° C. for 30 seconds, 72° C. for 30 seconds.

34. A method of amplifying *Toxoplasma gondii* DNA by polymerase chain reaction (PCR) using a pair of oligonucleotide primers, one oligonucleotide primer being specific for and complimentary to the ITS1 of *T. gondii*, and the other primer being complimentary to an ITS1 sequence common to Neospora and Toxoplasma species, wherein one primer includes the sequences SEQ ID NO:2 or SEQ ID NO:3, and the other primer includes the sequence SEQ ID NO:9.

35. The method according to claim 34 wherein the primers are SEQ ID NO:2 or SEQ ID NO:3 and SEQ ID NO:9 and the amplification utilizes standard PCR methods.

36. The method according to claim 35 wherein the amplified DNA product Using the primers SEQ ID NO:2 and SEQ NO:9 comprises approximately 144 bp and the amplified DNA product using the primers SEQ ID NO:3 and SEQ ID NO:9 comprises approximately 221 bp.

* * * * *